US008642794B1

(12) United States Patent
Kim et al.

(10) Patent No.: US 8,642,794 B1
(45) Date of Patent: Feb. 4, 2014

(54) **BIOSURFACTANT COMPOUNDS PRODUCED BY *AUREOBASIDIUM PULLULANS***

(71) Applicant: Gyeongbuk Institute for Marine Bio-industry, Gyeongsangbuk-do (KR)

(72) Inventors: Jong Shik Kim, Gyeongsangbuk-do (KR); Choong Gon Kim, Gyeongsangbuk-do (KR); Nyun Ho Park, Gyeongsangbuk-do (KR)

(73) Assignee: Gyeongbuk Institute for Marine Bio-Industry, Gyeongsangbuk-do (KR)

( * ) Notice: Subject to any disclaimer, the term of this patent is extended or adjusted under 35 U.S.C. 154(b) by 0 days.

(21) Appl. No.: 13/707,052

(22) Filed: Dec. 6, 2012

(30) Foreign Application Priority Data

Sep. 6, 2012 (KR) .......................... 10-2012-0098952

(51) Int. Cl.
C07C 59/147 (2006.01)
(52) U.S. Cl.
USPC ............... 554/121; 554/1; 554/115; 554/213; 510/211; 424/78.04; 514/844; 514/846
(58) Field of Classification Search
None
See application file for complete search history.

(56) References Cited

FOREIGN PATENT DOCUMENTS

| | | |
|---|---|---|
| JP | 06-158093 A | 6/1994 |
| KR | 10-2008-0017148 A | 2/2008 |
| KR | 10-2009-0131316 A | 12/2009 |
| KR | 10-2009-0131815 A | 12/2009 |

OTHER PUBLICATIONS

Ishigami, Yutaka et al.: "The pH-Sensitive Conversion of Molecular Aggregates of Rhamnolipid Biosurfactant", *Chemistry Letters*, pp. 763-766, 1987.
Doong, Ruey-an et al.: "Solubilization and mineralization of polycyclic aromatic hydrocarbons by *Pseudomonas putida* in the presence of surfactant", *Journal of Hazardous Materials*, B96 (2003), pp. 15-27.
Deshpande, S. et al.: "Surfactant Selection for Enhancing Ex Situ Soil Washing", *Wat. Res.*, vol. 33, No. 2, pp. 351-360, 1999.
Lee, Sang-Cheol et al.: "Characteristics of Biosurfactants produced by *Bacillus* sp. LSC11", *Korean Journal of Life Science*, vol. 12, No. 6, pp. 745-751, 2002. In Korean with English abstract.

*Primary Examiner* — Yate K Cutliff
(74) *Attorney, Agent, or Firm* — Frommer Lawrence & Haug LLP; Ronald R. Santucci

(57) ABSTRACT

Disclosed are novel compounds having biosurfactant activity that are produced by an *Aureobasidium pullulans* L-3-GPY strain. The chemical structure of the novel compounds having biosurfactant activity has been analyzed by using a spectrophotometer, and it has been confirmed that the compounds produced by the above strain show excellent surfactant activity.
The active ingredient of the biosurfactant according to the present invention can be applied in various fields such as a cleansing and purifying compositions. Further, the active ingredient of the biosurfactant can be used in numerous industrial fields where chemical surfactants have been conventionally used such as medical, foods, cosmetics, purification of oil contaminated land and seawater, milk fat degradation, and the like.

7 Claims, 19 Drawing Sheets

BIOSURFACTANT COMPOUNDS PRODUCED BY *AUREOBASIDIUM PULLULANS*

CROSS-REFERENCE TO RELATED APPLICATION

This application claims under 35 U.S.C. §119(a) the benefit of Korean Patent Application No. 10-2012-0098952 filed Sep. 6, 2012, the entire contents of which are incorporated herein by reference.

FIELD OF THE INVENTION

The present invention relates to novel biosurfactants produced by an *Aureobasidium* spp. strain.

BACKGROUND

The present invention relates to novel biosurfactant compounds that are produced by *Aureobasidium pullulans* sp. L-3-GPY as a biosurfactant producing microorganism.

Surfactants are usually organic compounds that contain both hydrophobic groups and hydrophilic groups within a molecule, and that lower the surface tension of a liquid by modifying surface or interfacial properties. If a water phase is present, surfactants act by weakening the binding of water molecules to one another. At a concentration level known as the critical micelle concentration, surfactant molecules form a micelle structure in which hydrophobic groups are located on the outside of the structure and hydrophilic groups are located on the inside thereof. In a hydrophobic solution, such as a hydrocarbon solution, surfactants form an emulsion. Surfactants are characterized by having physical properties such as dispersibility, emulsifiability, permeability, wettability and bubble-forming capability. It has been reported that surfactants increase desorption and solubility of hydrocarbons, leading to biodegradation thereof by microorganisms (Deshpande et al., 1999. Water Res., 33, 351-360; Doong and Lei, 2003. J. Hazard Mater., 96, 15-27).

While in the past surfactants have been synthesized from oils and fats in small quantities, currently chemical surfactants have been mass-produced from coal, petroleum, and the like. Additionally, chemical surfactants are currently used in various industrial fields including electronics, construction, mechanics, printing, papers, fibers, and the like. However, chemical surfactants can be problematic for several reasons. First, they are very difficult to make due to their complex manufacturing process. Also, they threaten aquatic ecosystems because they form bubbles on the surface of water, thereby blocking necessary sunlight and oxygen, and they produce toxic inorganic phosphates from organic phosphorus added to the chemical surfactants to enhance their detergency. Further, because of their extremely low biodegradability, chemical surfactants accumulate in ecosystems, exhibiting strong toxicity, and causing serious environmental pollution. By contrast, biosurfactants produced in vivo or in vitro by microorganisms, such as yeasts, fungi or bacteria, are more eco-friendly materials compared to chemical surfactants, in that they are non-toxic and biodegradable (Lee et al, 2002. Kor. J. lifescience, 12, 745-751). Furthermore, although biosurfactants have complex chemical structures that are difficult to synthesize according to conventional methods, they are still very useful compounds that could be used for specific purposes. In addition, biosurfactants produce nearly the same effects as conventional chemical surfactants on the physical and chemical properties of a solution including surface tension reduction and temperature/pH stabilization, and thus, they are very valuable materials (Ishigami et al., 1987. Chem. Lett., 763).

Biosurfactants, like chemical surfactants, can be widely used in various industrial fields such as medicine, foods, cosmetics, cleaning materials, secondary oil recovery, pulp and papers, purification of oil-contaminated land and seawater, milk fat degradation, and the like.

Since pure water has a surface tension of 72 dyne/cm or higher, and its surface tension is decreased in the presence of surfactants, surfactant concentration and activity levels are generally determined by a decrease in the surface tension of pure water. Thus, the activity of biosurfactants produced by microorganisms can be determined by measuring the surface tension of a microorganism culture solution. Generally, it has been confirmed that if the surface tension of a microbial culture solution is lower than 40 dyne/cm, then the microorganisms produce some biosurfactants, and if the surface tension is lower than 35 dyne/cm, then the microorganisms produce biosurfactants in large quantities. Therefore, microorganism cultures that are widely used in industry are those that effect a surface tension of 30 to 35 dyne/cm. It has been reported that the microorganism strain, *Bacillus subtillis*, effects a surface tension of 27 to 28 dyne/cm (strongest reported surface activity) when cultured in a blood agar medium.

In addition, the *Aureobasidium* spp. strain has been known to produce beta-glucans. Beta-glucans a type of polysaccharide, potentially enhance cell immune function, and occur most commonly as cellulose in plants, cereal grain bran, cell walls of baker's yeast, and certain fungi, mushrooms and bacteria. Beta-glucans can activate immune function of normal human cells, suppress the proliferation and recurrence of cancer cells, decrease blood glucose and cholesterol levels, improve lipid metabolism, and prevent body fat from forming and accumulating.

However, there has been no report that an *Aureobasidium pullulans* strain can produce biosurfactant materials.

SUMMARY OF THE INVENTION

Therefore, the present inventors have selected compounds having surface activity from various materials produced by an *Aureobasidium pullulans* L-3-GPY deposited under Accession No. KCCM11200P, and confirmed that they are novel compounds capable of being used as biosurfactants.

Therefore, the object of the present invention is to provide compounds produced by *Aureobasidium pullulans* L-3-GPY deposited under Accession No. KCCM11200P.

Further, another object of the present invention is to provide the use of the compounds produced by the *Aureobasidium pullulans* strain as a biosurfactant.

Other objectives and advantages of the present invention will be apparent upon consideration of the following specification, with reference to the accompanying drawings and claims.

It is an objective of the present invention to provide a compound represented by the following Formula 1 which is produced by *Aureobasidium pullulans* L-3-GPY deposited under Accession No. KCCM11200P.

[Formula 1]

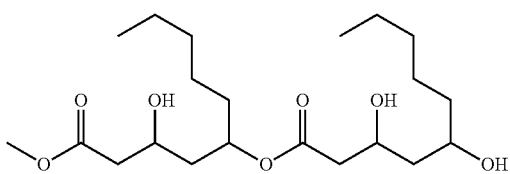

It is another objective of the present invention to provide a compound represented by the following Formula 2 which is produced by *Aureobasidium pullulans* L-3-GPY deposited under Accession No. KCCM11200P.

[Formula 2]

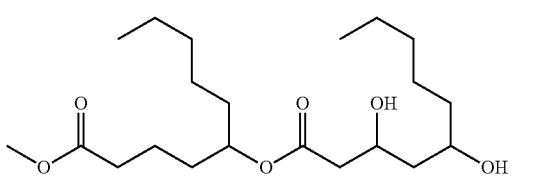

It is still another objective of the present invention to provide a cleansing and purifying composition comprising the biosurfactants of the above Formula 1 and Formula 2.

EFFECT OF THE INVENTION

The features and advantages of the present invention are summarized as follows:

(i) the compounds having biosurfactant activities that are produced by *Aureobasidium pullulans* L-3-GPY are novel compounds, and (ii) since the compounds produced by *Aureobasidium pullulans* L-3-GPY have excellent surfactant activity, they can be effectively used as a cleansing and purifying composition, and can be applied to various industrial fields where chemical surfactants have been widely used such as medical, foods, cosmetics, purification of oil contaminated land and seawater, milk fat degradation, and the like.

DETAILED DESCRIPTION OF THE INVENTION

Figure 1:
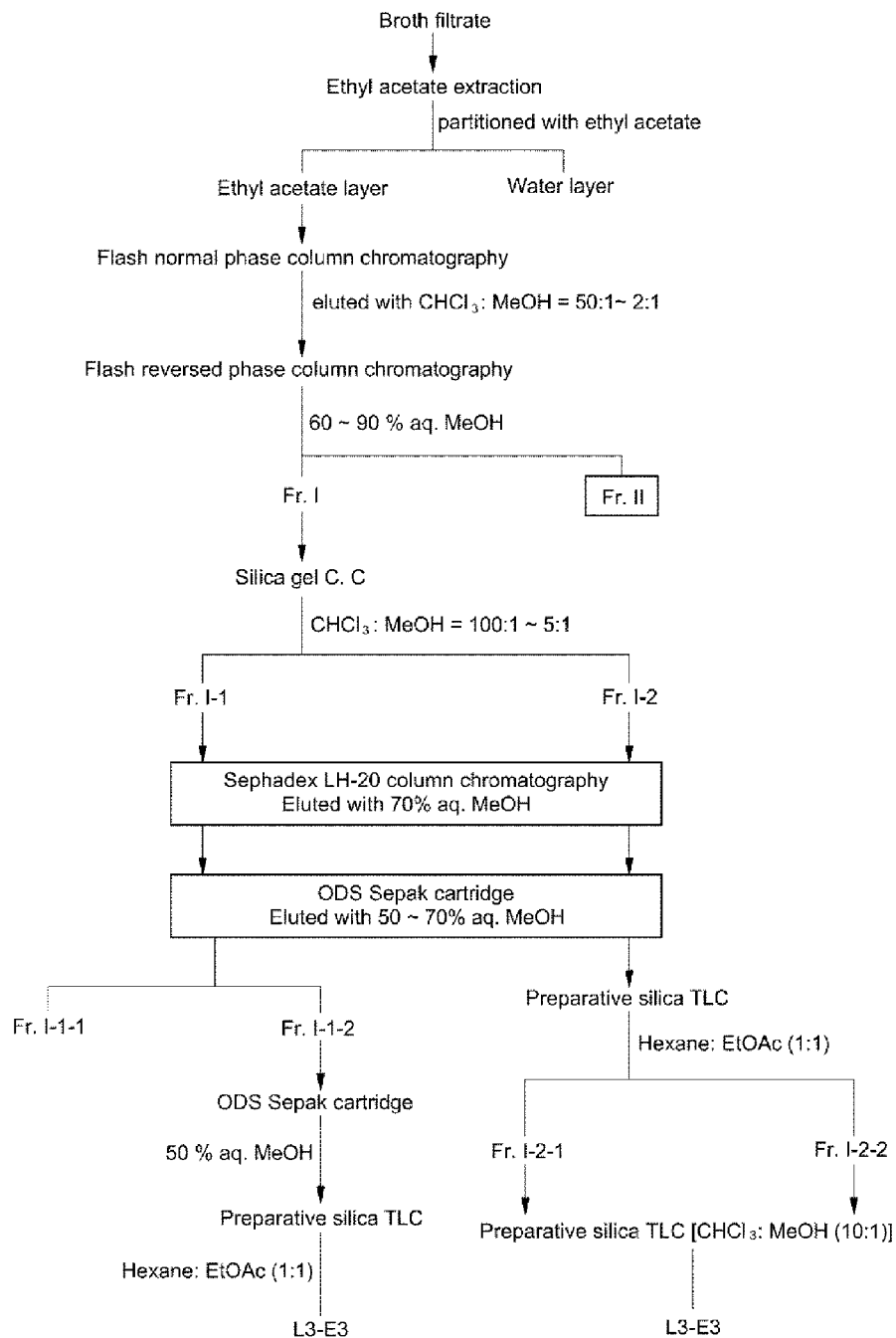
FIG. 1 is a diagram showing the isolation and purification of an active compound L3-E3 from a fraction Fr. I.

Hereinafter, the present invention will be described in more detail.

According to one aspect of the present invention, a compound represented by the following Formula 1 is provided, which is produced by *Aureobasidium pullulans* L-3-GPY deposited under Accession No. KCCM11200P.

[Formula 1]

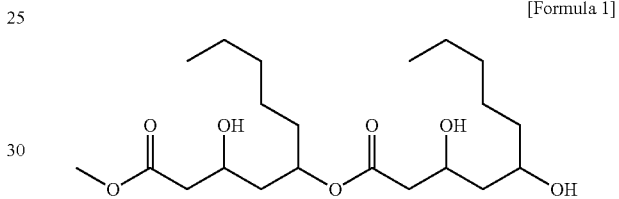

According to another aspect of the present invention, a compound represented by the following Formula 2 is provided, which is produced by *Aureobasidium pullulans* L-3-GPY deposited under Accession No. KCCM11200P.

[Formula 2]

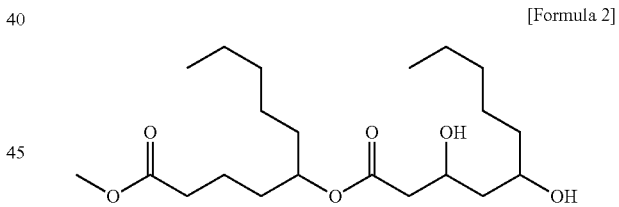

According to an exemplary embodiment of the present invention, the compound having the structure of Formula 1 is a biosurfactant. As used herein, the term "biosurfactants" refers to surface-active substances synthesized by living cells and are usually organic compounds (that is, lipids or derivatives thereof) that are amphiphilic, meaning they contain both hydrophobic and hydrophilic groups. A "biosurfactant" is a comprehensive term including all kinds of organism-derived surfactant materials, but generally refers to a surfactant material synthesized by a microorganism. Biosurfactants have lower toxicity and higher biodegradability as compared with conventional synthetic surfactants, which makes it possible to overcome problems such as environmental pollution. Furthermore, although biosurfactants have complex chemical structures that are difficult to synthesize according to conventional methods, they are still very useful compounds that could be used for specific purposes. In addition, biosurfactants produce nearly the same effects as conventional chemical surfactants on the physical and chemical properties of a solution including surface tension reduction and temperature/pH stabilization, and thus, they are very valuable materials (Ishigami et al., 1987. Chem. Lett., 763).

According to an exemplary embodiment, the present invention provides a cleansing and purifying composition comprising the biosurfactant which comprises the compound represented by Formula 1, the compound represented by Formula 2, or a mixture thereof. Further, the biosurfactant of the present invention can be effectively used in various industrial fields where chemical surfactants have been used such as medical, foods, cosmetics, cleaning materials, secondary oil recovery, pulp and papers, purification of oil contaminated land and seawater, milk fat degradation and the like, but are not limited thereto.

The present invention is further illustrated by the following examples. However, it shall be understood that these examples are only to be used to specifically set forth the present invention, and they are not to be used to limit the present invention in any form.

EXAMPLE 1

Isolation and Purification of Active Fractions Fr. I-1-1 and Fr. I-1-2 from *Aureobasidium pullulans* L-3-GPY Strain The present invention is characterized by using *Aureobasidium pullulans* L-3-GPY which has been deposited under Accession No. KCCM11200P at Korean Culture Center of Microorganisms (KCCM) on Jul. 5, 2011.

A freeze-dried culture supernatant of *Aureobasidium pullulans* L-3-GPY (about 100 kg) was dissolved in water, followed by ethyl acetate (200 L) extraction and liquid-liquid partitioning twice. After an ethyl acetate phase was concentrated under reduced pressure, it was subjected to flash normal phase (silica gel) column chromatography using an eluting solvent of chloroform:methanol (50:1→2:1, v/v) (FIG. 1).

A chloroform:methanol (50:1, v/v) fraction showing strong desired activities was concentrated, followed by flash reversed-phase (ODS, $C_{18}$) column chromatography using an eluting solvent of 60%→90% aqueous methanol. As a result, two active fractions Fr. I (fraction eluted with 80% aqueous methanol) and Fr. II (fraction eluted with 90% aqueous methanol) were collected. First, the fraction Fr. I was concentrated under reduced pressure and subjected to silica gel column chromatography using an eluting solvent of chloroform:methanol (100:1→10:1, v/v). As a result, fractions Fr. I-1 and Fr. I-2 showing desired activities were harvested (FIG. 1).

After the fraction Fr. I-1 was concentrated, it was subject to Sephadex LH-20 column chromatography using 70% aqueous methanol. Thus obtained active fractions were concentrated and analyzed with reversed-phase (ODS, $C_{18}$) Sepak cartridge chromatography using 50%→70% aqueous methanol. As a result, active fractions Fr. I-1-1 and Fr. I-1-2 were collected.

EXAMPLE 2

Isolation and Purification of Compound L3-E3 from Fr. I-1-2 Fraction

The fraction Fr. I-1-2 was subjected to reversed-phase (ODS, $C_{18}$) Sepak cartridge chromatography using 50% aqueous methanol and preparative silica gel TLC (hexane:ethyl acetate=1:1, v/v), to thereby purify the compound L3-E3.

Among them, the compound L3-E3 showed almost the same Rf values on a silica gel TLC plate, which was carried out using chloroform:methanol (10:1, v/v) as the solvent. However, compound L3-E3 showed significantly different Rf values on a silica gel TLC plate, which was carried out using hexane:ethyl acetate (1:1, v/v) as the solvent.

EXAMPLE 3

Isolation and Purification of Active Fraction Fr. II from *Aureobasidium pullulans* L-3-GPY As disclosed in Example 1, a freeze-dried culture supernatant of *Aureobasidium pullulans* L-3-GPY (about 100 kg) was dissolved in water, followed by ethyl acetate (200 L) extraction and liquid-liquid partitioning twice. After an ethyl acetate phase was concentrated under reduced pressure, it was subjected to flash normal phase (silica gel) column chromatography using an eluting solvent of chloroform:methanol (50:1→2:1, v/v) (FIG. 1).

A chloroform:methanol (50:1, v/v) fraction showing strong desired activities was concentrated, followed by flash reversed-phase (ODS, $C_{18}$) column chromatography using an eluting solvent of 60%→90% aqueous methanol. As a result, two active fractions Fr. I (fraction eluted with 80% aqueous methanol) and Fr. II (fraction eluted with 90% aqueous methanol) were collected.

First, the fraction Fr. I was concentrated under reduced pressure and subject to silica gel column chromatography using an eluting solvent of chloroform:methanol (100:1→10:1, v/v). As a result, fractions Fr. I-1 and Fr. I-2 showing desired activities were harvested (FIG. 1).

Among them, a chloroform:methanol (50:1, v/v) fraction showing strong desired activities was concentrated and subjected to flash reversed-phase (ODS, $C_{18}$) column chromatography using an eluting solvent of 60%→90% aqueous methanol. As a result, two active fractions Fr. I (fraction eluted with 80% aqueous methanol) and Fr. II (fraction eluted with 90% aqueous methanol) were collected.

Figure 2:
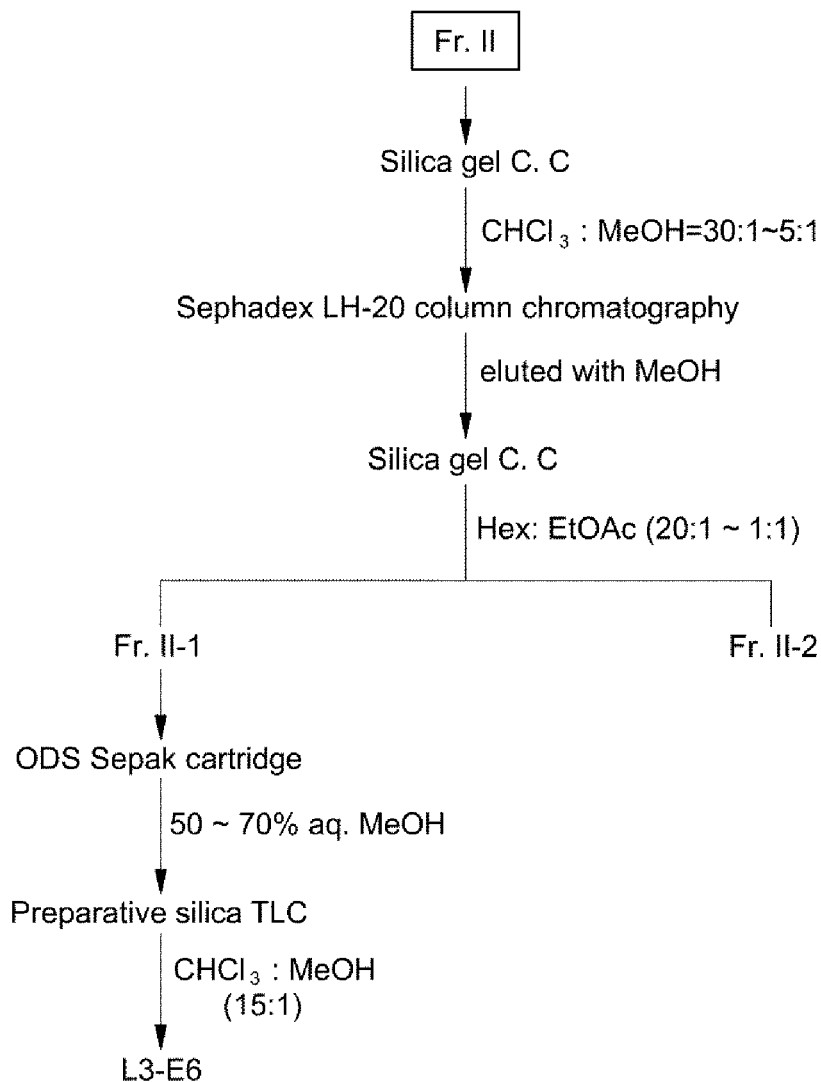
FIG. 2 is a diagram showing the isolation and purification of an active compound L3-E6 from a fraction Fr. II.

The fraction Fr. II was subject to silica gel column chromatography using an elution solvent of chloroform:methanol (30:1→5:1, v/v), concentrated under reduced pressure, and then subjected to Sephadex LH-20 column chromatography using an eluting solvent of methanol (FIG. 2). The obtained active fraction was then concentrated under reduced pressure, followed by silica gel column chromatography using an eluting solvent of hexane:ethyl acetate (20:1→1:1, v/v). As a result, two active fractions Fr. II-1 and Fr. II-2 were collected.

EXAMPLE 4

Isolation and Purification of Compound L3-E6 from Fr. II-1 Fraction

The fraction Fr. II-1 was subjected to ODS Sepak cartridge chromatography using an eluting solvent of 50~70% aqueous methanol and preparative silica TLC using an eluting solution of chloroform:methanol (15:1, v/v), to thereby isolate and purify the compound L3-E6.

EXAMPLE 5

Chemical Structure Analysis of Active Compound L3-E3 by Spectroscopy

1) Measurement and Interpretation of NMR Spectrum

In order to investigate the chemical structure of the active compound L3-E3, the compound was dissolved in $CDCl_3$, and its $^1H$ NMR, $^{13}C$ NMR, $^1H$-$^1H$ COSY, HMQC and HMBC spectra were measured and interpreted.

Figure 3:
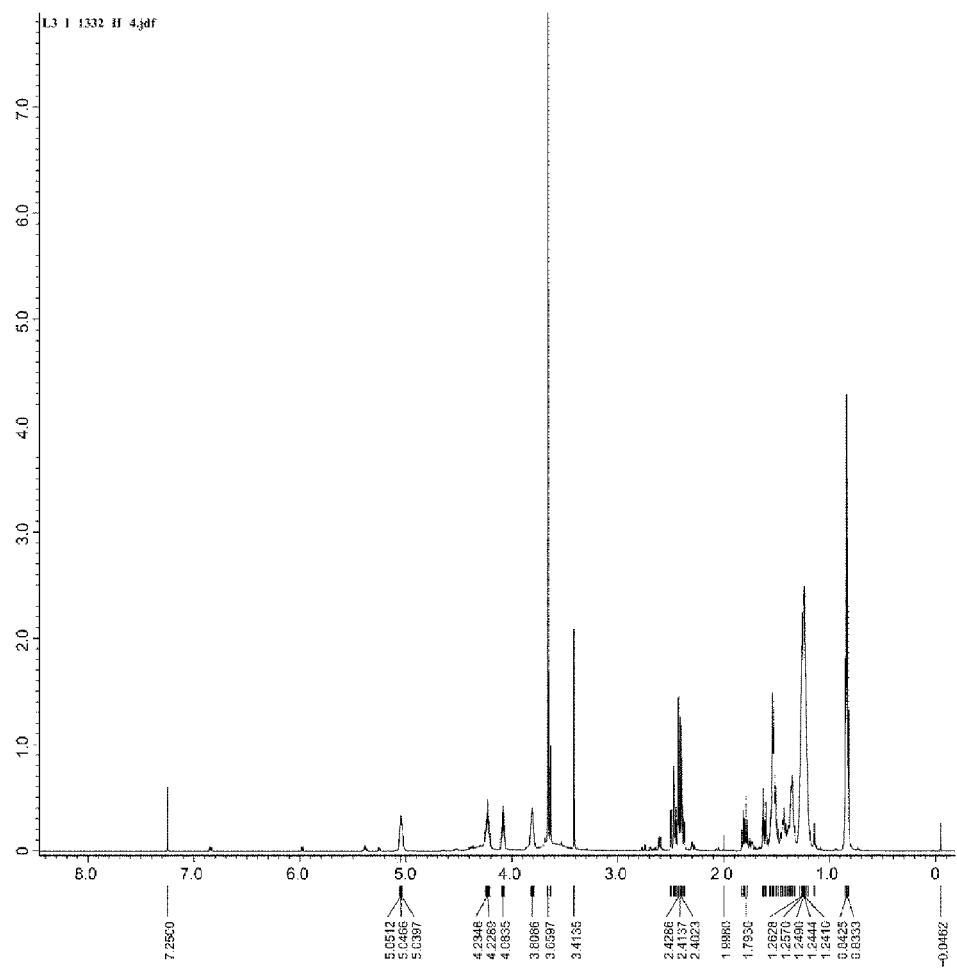
FIG. 3 is a $^1$H NMR spectrum of a compound L3-E3.

① Measurement and Interpretation of $^1H$ NMR Spectrum:

As a result of measuring a $^1H$ NMR spectrum (FIG. 3), four oxygenated methine signals were observed at 5.05, 4.23, 4.08 and 3.81 ppm, one methoxy proton signal was observed at 3.66 ppm, twelve methylene proton signals were observed at 2.47/2.41, 2.42, 1.80/1.62, 1.53(×2), 1.43/1.37, 1.37/1.26, 1.26/1.24, 1.25(×4) ppm, and two methyl proton signals were observed at 0.84 ppm.

Figure 4:
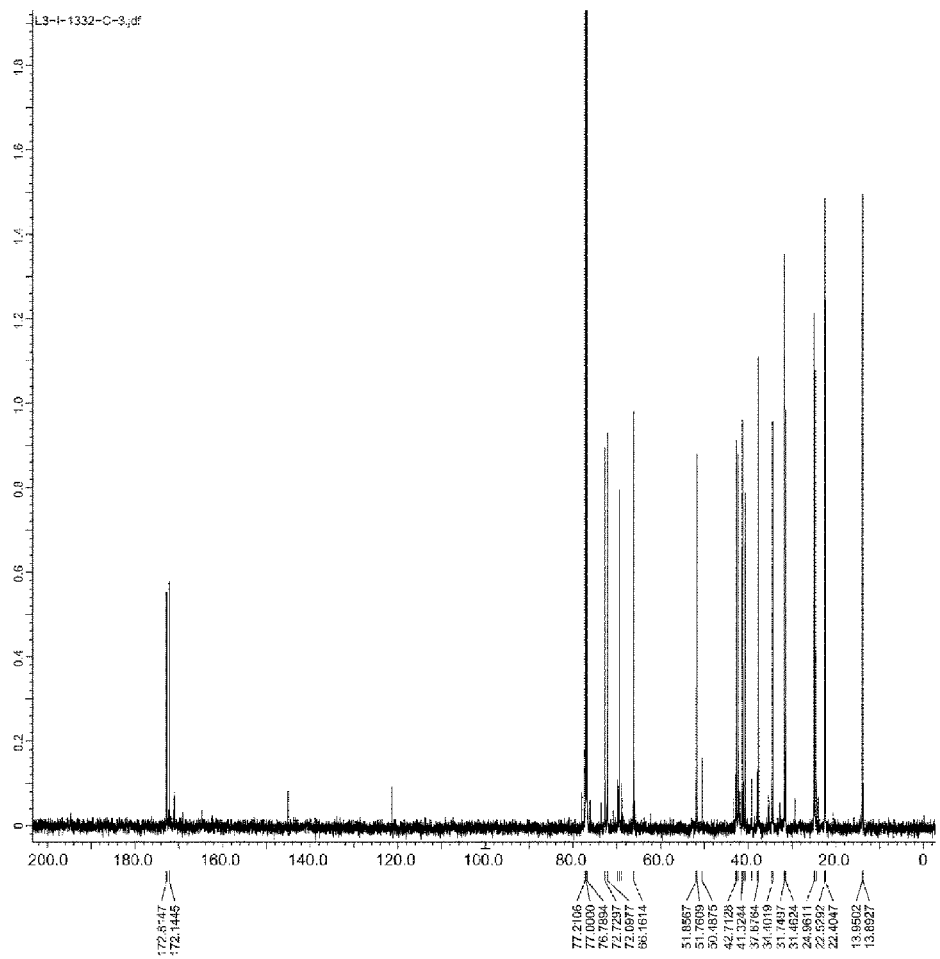
FIG. 4 is a $^{13}$C NMR spectrum of a compound L3-E3.

② Measurement and Interpretation of $^{13}C$ NMR Spectrum:

As a result of measuring a $^{13}C$ NMR spectrum (FIG. 4), total 21 carbon signals were observed. In particular, two ester carbonyl carbon signals were observed at 172.8 and 172.1 ppm, four oxygenated methine carbon signals were observed at 72.7, 72.1, 69.5 and 66.2 ppm, one methoxy carbon signal was observed at 51.8 ppm, twelve methylene carbon signals were observed at 42.7, 42.3, 41.3, 40.7, 37.7, 34.4, 31.7, 31.5, 25.0, 24.7, 22.5 and 22.4 ppm, and two methyl carbon signals were observed at 14.0 and 13.9 ppm.

Figure 5:
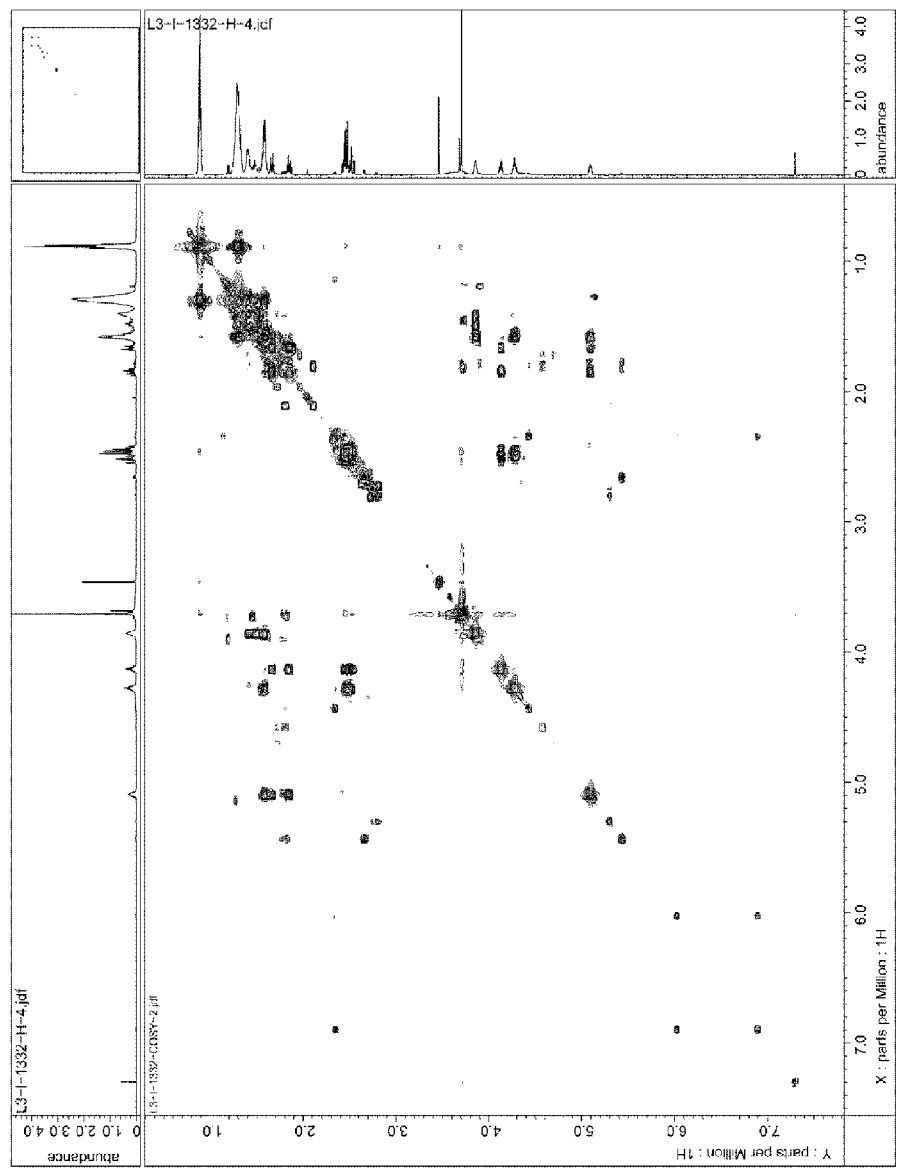
FIG. 5 is a $^1$H-$^1$H COSY spectrum of a compound L3-E3.
Figure 6:
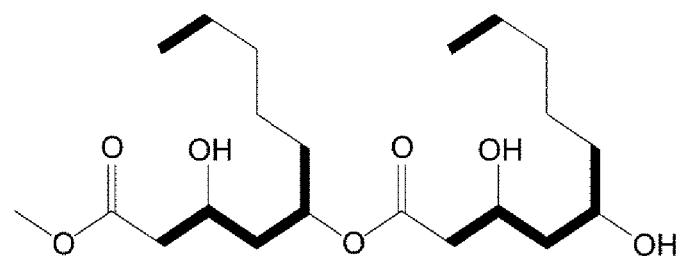
FIG. 6 is a partial structure of a compound L3-E3 identified from the $^1$H-$^1$H COSY spectrum.

③ Measurement and Interpretation of $^1H$-$^1H$ COSY Spectrum:

In order to investigate a partial structure of the compound L3-E3, a $^1H$-$^1H$ COSY spectrum capable of identifying $^3J_{H-H}$ correlation was measured and interpreted (FIG. 5). As a result, four partial structures of —$CH_2$—CH(—OH)—$CH_2$—CH(—OH)—$CH_2$—, —$CH_2$—CH(—OH)—$CH_2$—CH(—OH)—$CH_2$—, $CH_3$—$CH_2$—, and $CH_3$—$CH_2$— were identified (FIG. 6).

Figure 7:
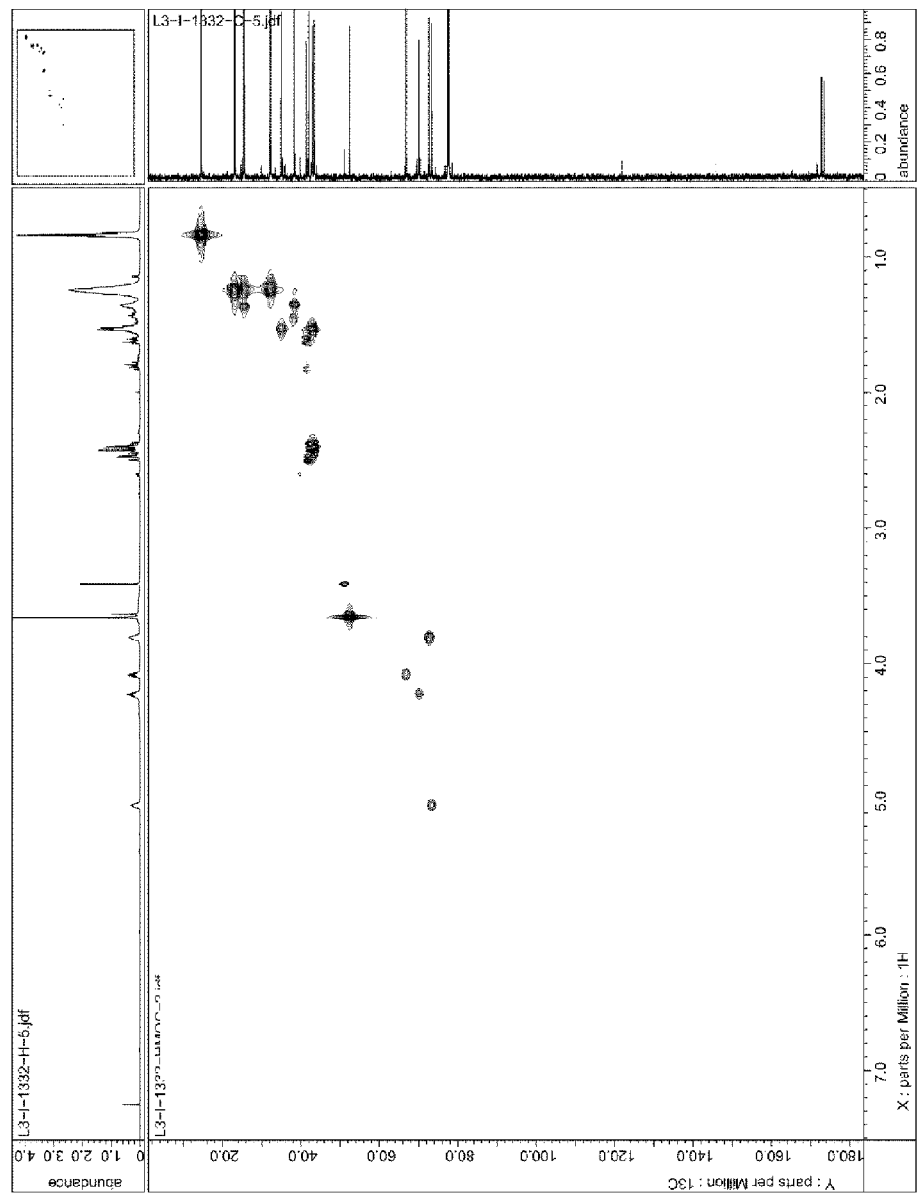
FIG. 7 is a HMQC spectrum of a compound L3-E3.

④ Measurement and Interpretation of HMQC and HMBC Spectra:

As a result of measuring a HMQC spectrum (FIG. 7), all proton-bearing carbons ($^1J_{C-H}$) were identified.

Figure 8:
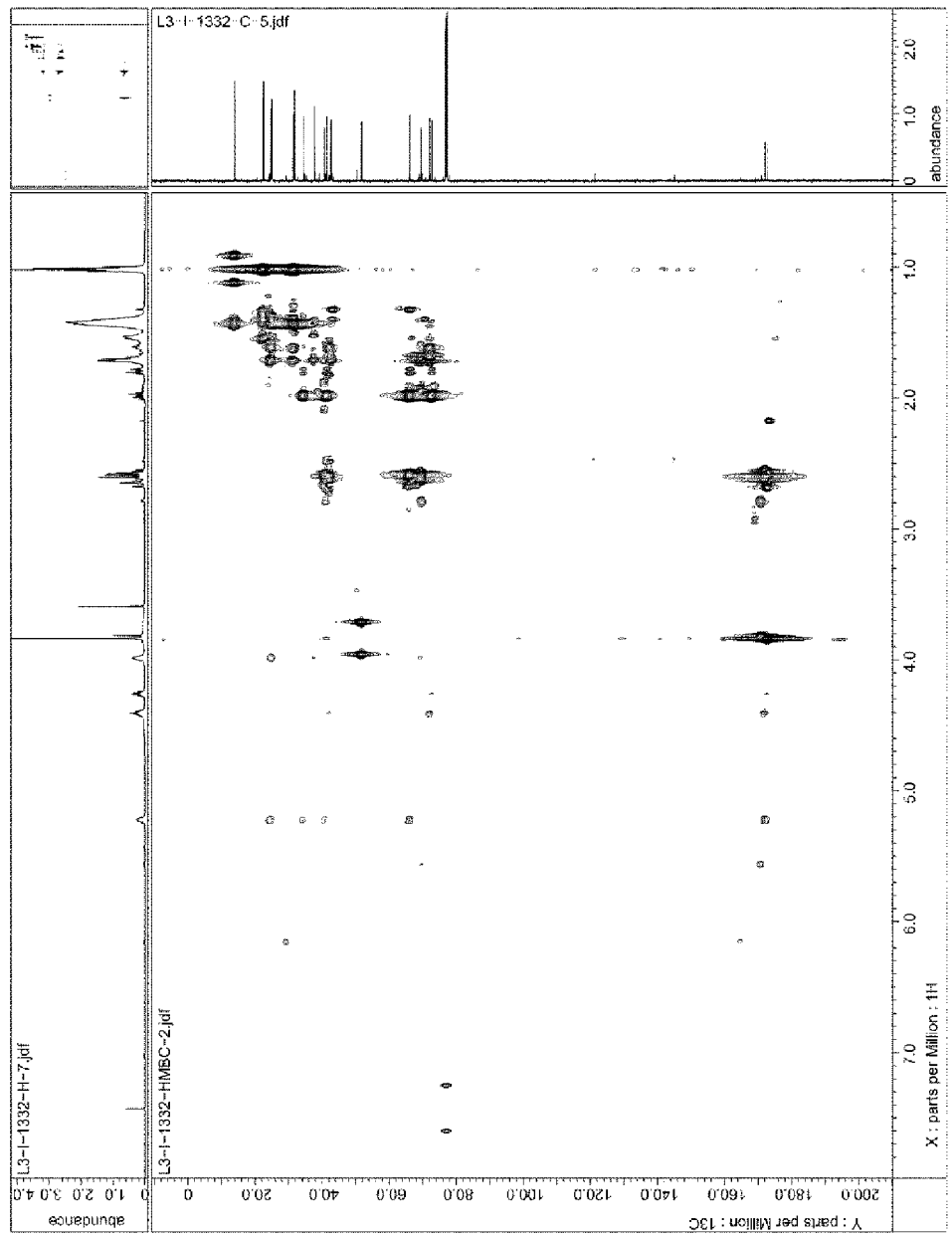
FIG. 8 is a HMBC spectrum data of a compound L3-E3.
Figure 9:
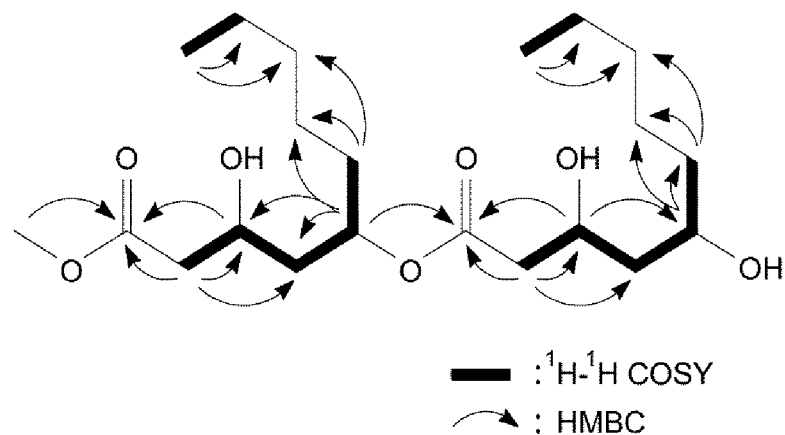
FIG. 9 is a chemical structure of a compound L3-E3 identified from the HMBC spectrum.
Figure 10:
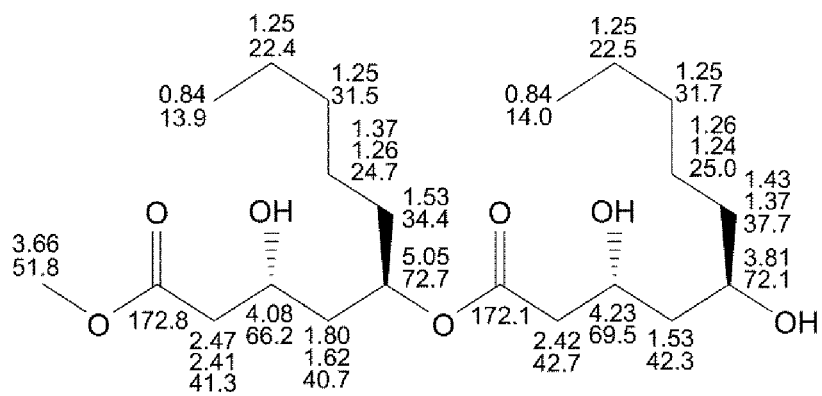
FIG. 10 is assignment values of $^1$H NMR and $^{13}$C NMR peaks of a compound L3-E3.

Further, as a result of measuring a HMBC spectrum (FIG. 8), a long-range correlation with an ester carbonyl carbon signal at 172.8 ppm was observed from a methoxy proton signal at 3.66 ppm and a methylene proton signal at 2.47/2.41 ppm, and a long-range correlation with an ester carbonyl carbon signal at 172.1 ppm was observed from an oxygenated methine proton signal at 5.05 ppm, a methylene proton signal at 2.42 ppm and an oxygenated methine proton signal at 4.23 ppm. In two propyl partial structures, a long-range correlation with methylene carbon signals at 31.5 and 24.7 ppm was observed from a methylene proton signal at 1.53 ppm, and that with methylene carbon signals at 31.7 and 25.0 ppm was observed from a methylene proton signal at 1.43 ppm, which confirmed a binding site. From these results, the chemical structure of the compound L3-E3 was determined as illustrated in FIG. 9. FIG. 10 shows the reversion reaction of proton and carbon peaks of the compound L3-E3.

2) Measurement and Interpretation of Mass Spectrum

Figure 11:
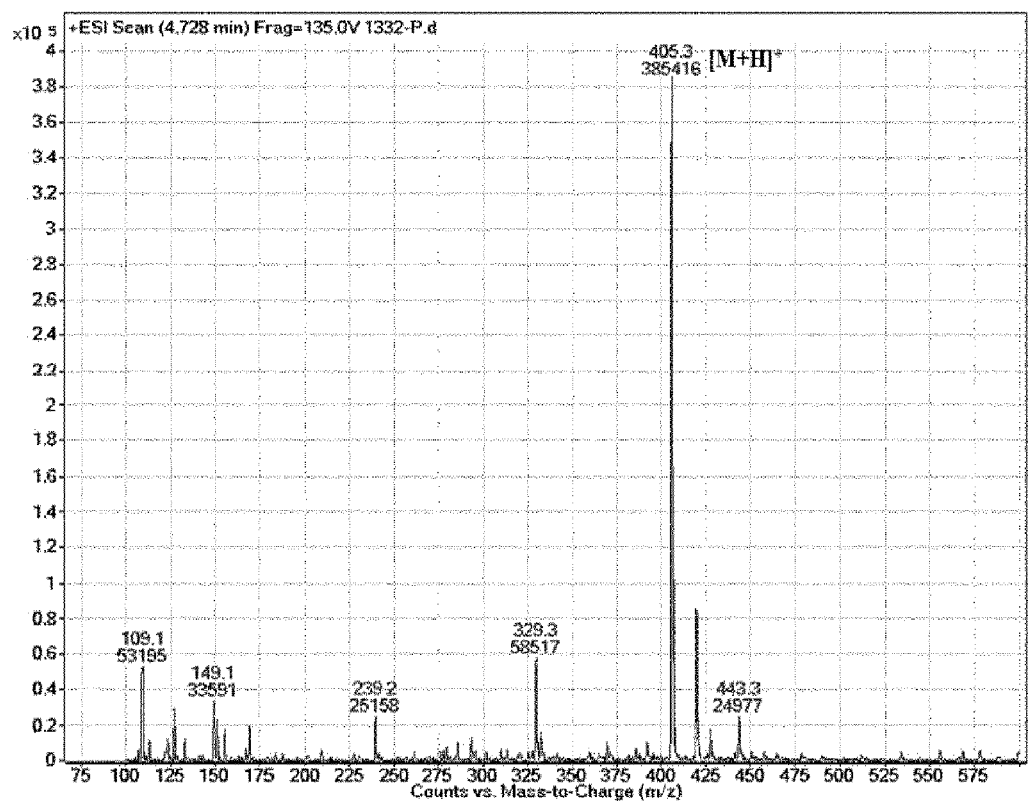
FIG. 11 is an ESI-mass spectrum of a compound L3-E3.

The chemical structure of the present active compound was identified by NMR spectroscopy. For this confirmation, mass spectroscopy analysis was carried out, and thus obtained results are as follows. As a result of measuring an ESI-mass spectrum in negative mode (FIG. 11), $[M+H]^+$ was observed at m/z 405.3, which suggests that the compound has a molecular weight of 404. This result corresponded to the chemical structure determined by the NMR spectroscopy (Molecular Formula: $C_{21}H_{40}O_7$).

EXAMPLE 6

Chemical Structure Analysis of Active Compound L3-E6 by Spectroscopy

1) Measurement and Interpretation of NMR Spectrum

Likewise, in order to investigate the chemical structure of the compound L3-E6, it was dissolved in $CDCl_3$, and its $^1H$ NMR, $^{13}C$ NMR, $^1H$-$^1H$ COSY, HMQC and HMBC spectra were measured and interpreted.

Figure 12:
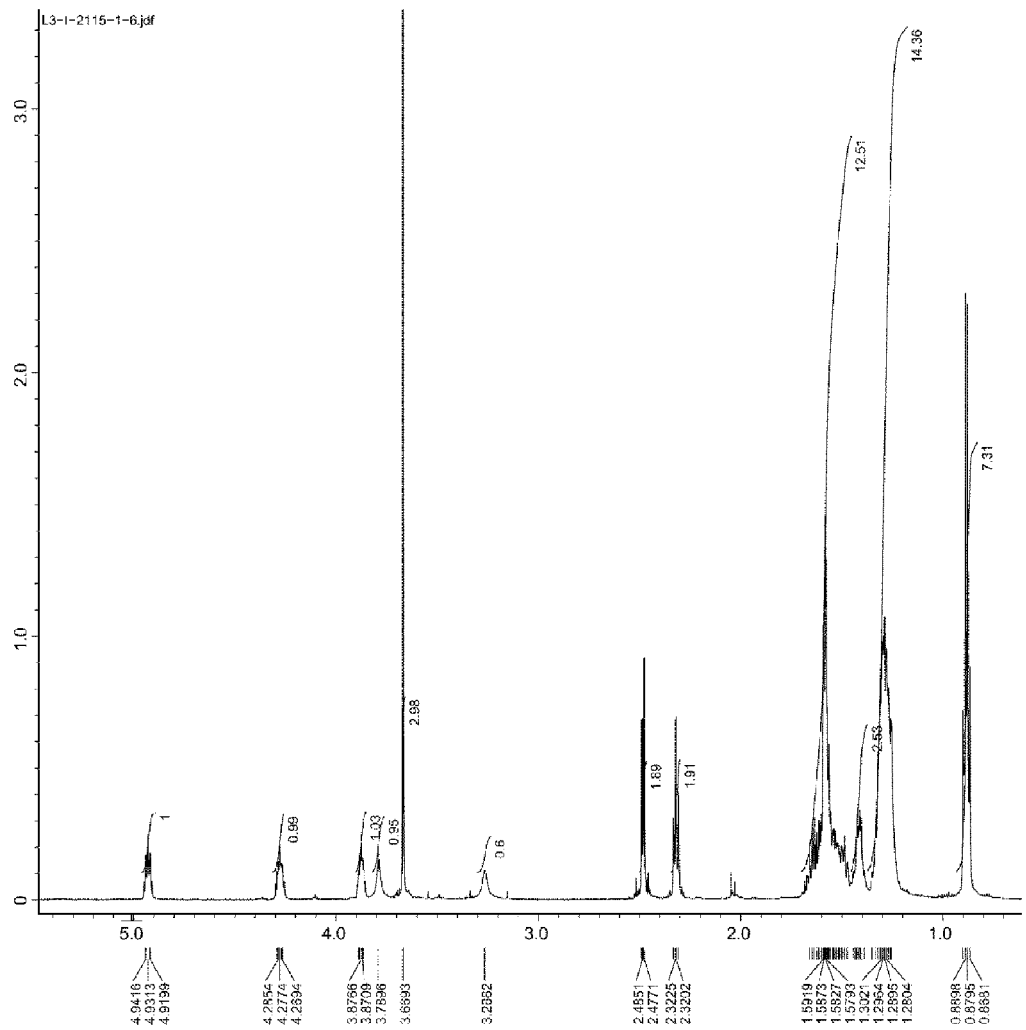
FIG. 12 is a $^1$H NMR spectrum of a compound L3-E6.

① Measurement and Interpretation of $^1H$ NMR Spectrum:

As a result of measuring a $^1H$ NMR spectrum (FIG. 12), three oxygenated methine signals were observed at 4.93, 4.28 and 3.88 ppm, one methoxy proton signal was observed at 3.67 ppm, thirteen methylene signals were observed at 2.48, 2.32, 1.64/1.59, 1.57, 1.53, 1.50/1.42, 1.45, 1.30(×2) and 1.29(×4) ppm, and two methyl proton signals were observed at 0.89 and 0.88 ppm. These results suggest that the compound L3-E6 is a dimer having a similar structure to the compound L3-E3.

Figure 13:
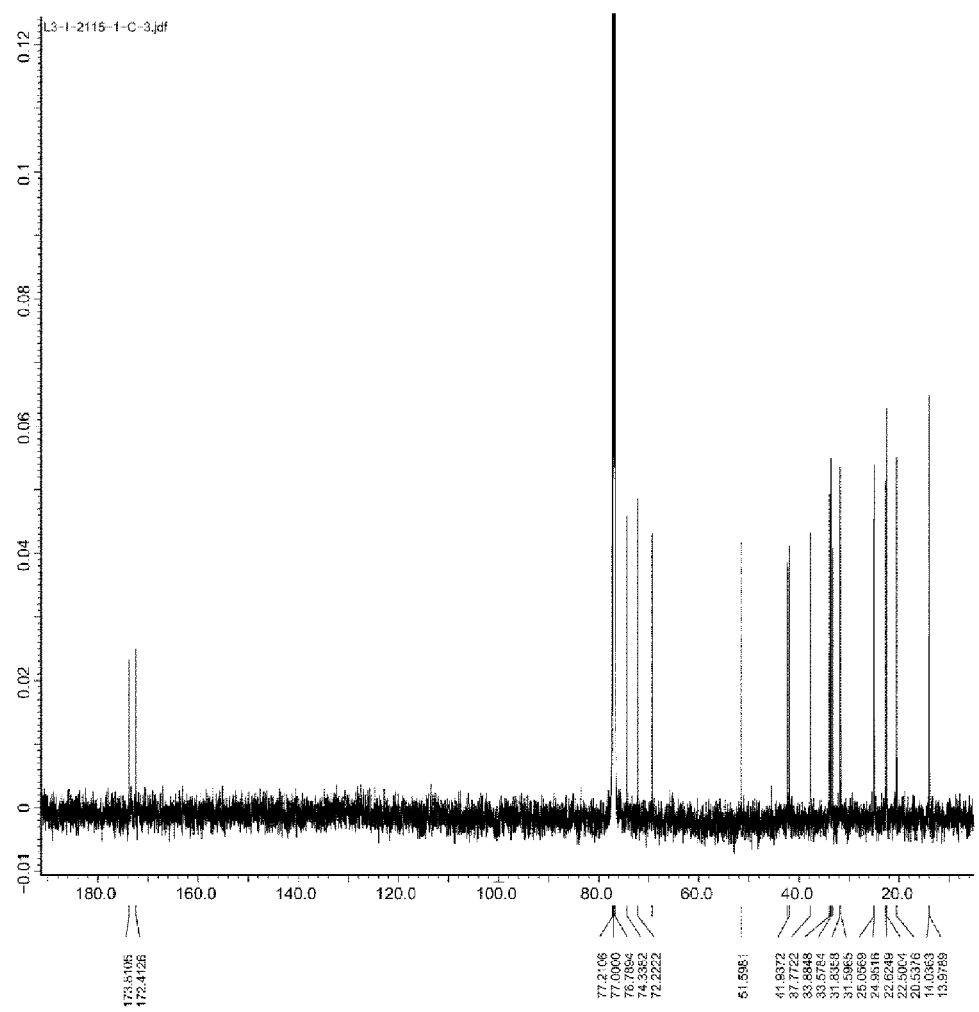
FIG. 13 is $^{13}$C NMR spectrum of a compound L3-E6.

② Measurement and Interpretation of $^{13}C$ NMR Spectrum:

As a result of measuring a $^{13}C$ NMR spectrum (FIG. 13), total 21 carbon siganls were observed. In particular, two ester carbonyl carbon signals were observed at 173.8 and 172.4 ppm, three oxygenated methine carbon signals were observed at 74.3, 72.2 and 69.2 ppm, one methoxy carbon signal was observed at 51.6 ppm, thirteen methylene carbon signals were observed at 42.3, 41.9, 37.8, 33.6, 33.9, 33.3, 31.8, 31.6, 25.1, 25.0, 22.6, 22.5 and 20.5 ppm, and two methyl carbon signals were observed at 14.0 ppm.

Figure 14:
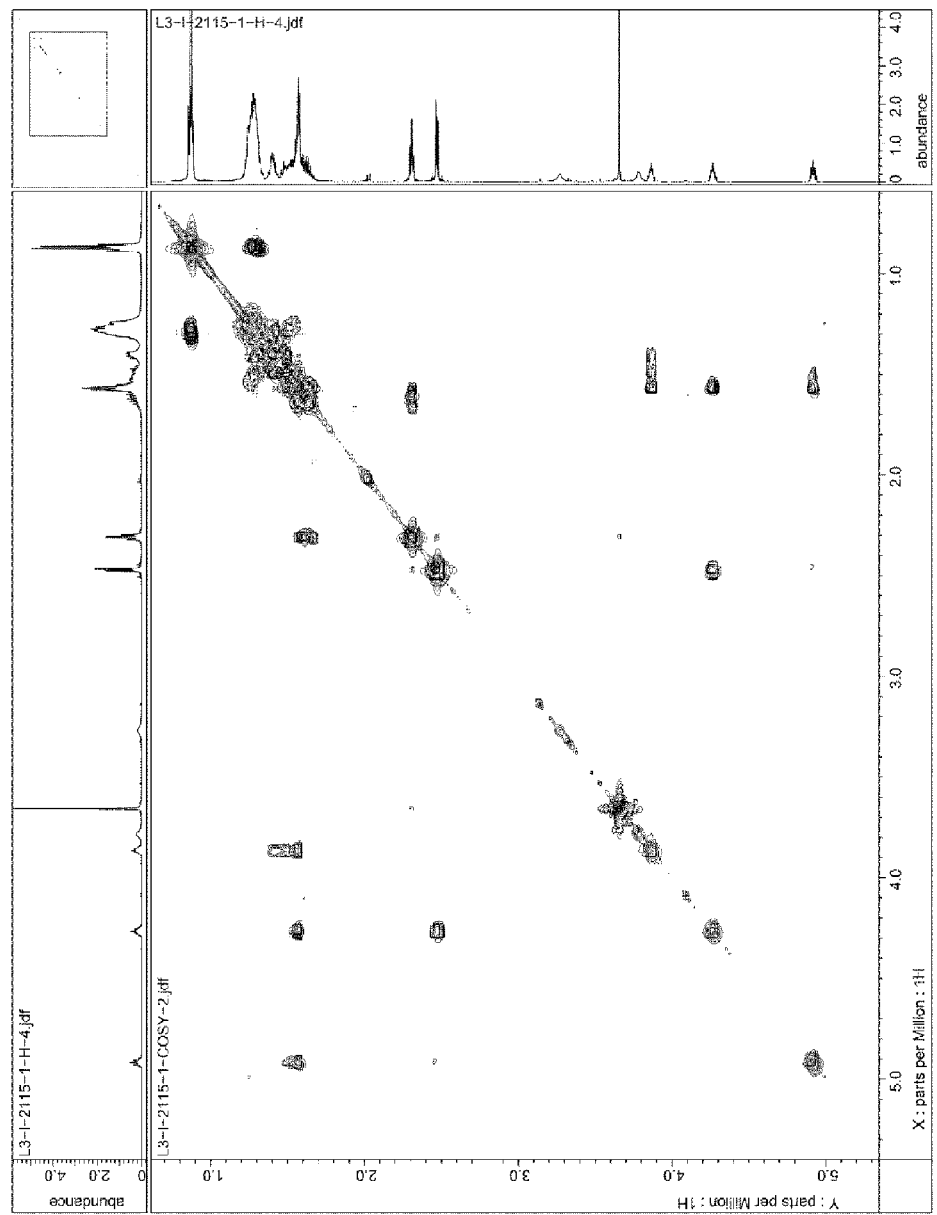
FIG. 14 is a $^1$H-$^1$H COSY spectrum of a compound L3-E6.
Figure 15:
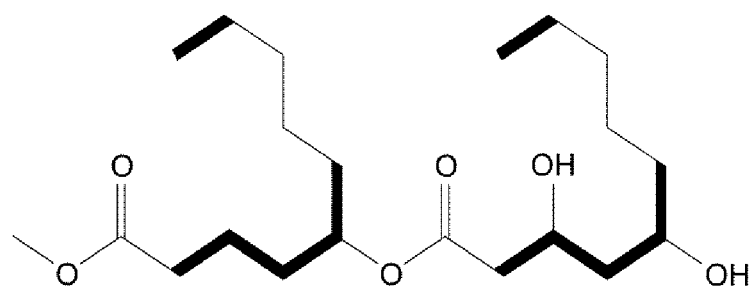
FIG. 15 is a partial structure of a compound L3-E6 identified from the $^1$H-$^1$H COSY spectrum.

③ Measurement and Interpretation of $^1H$-$^1H$ COSY Spectrum:

In order to investigate a partial structure of the compound L3-E6, a $^1H$-$^1H$ COSY spectrum capable of identifying $^3J_{H-H}$ correlation was measured and interpreted (FIG. 14). As a result, four partial structures of $CH_2$—$CH_2$—$CH_2$—CH(—OH)—$CH_2$—, —$CH_2$—CH(—OH)—$CH_2$—CH(—OH)—$CH_2$—, $CH_3$—$CH_2$—, and $CH_3$—$CH_2$— were identified (FIG. 15).

Figure 16:
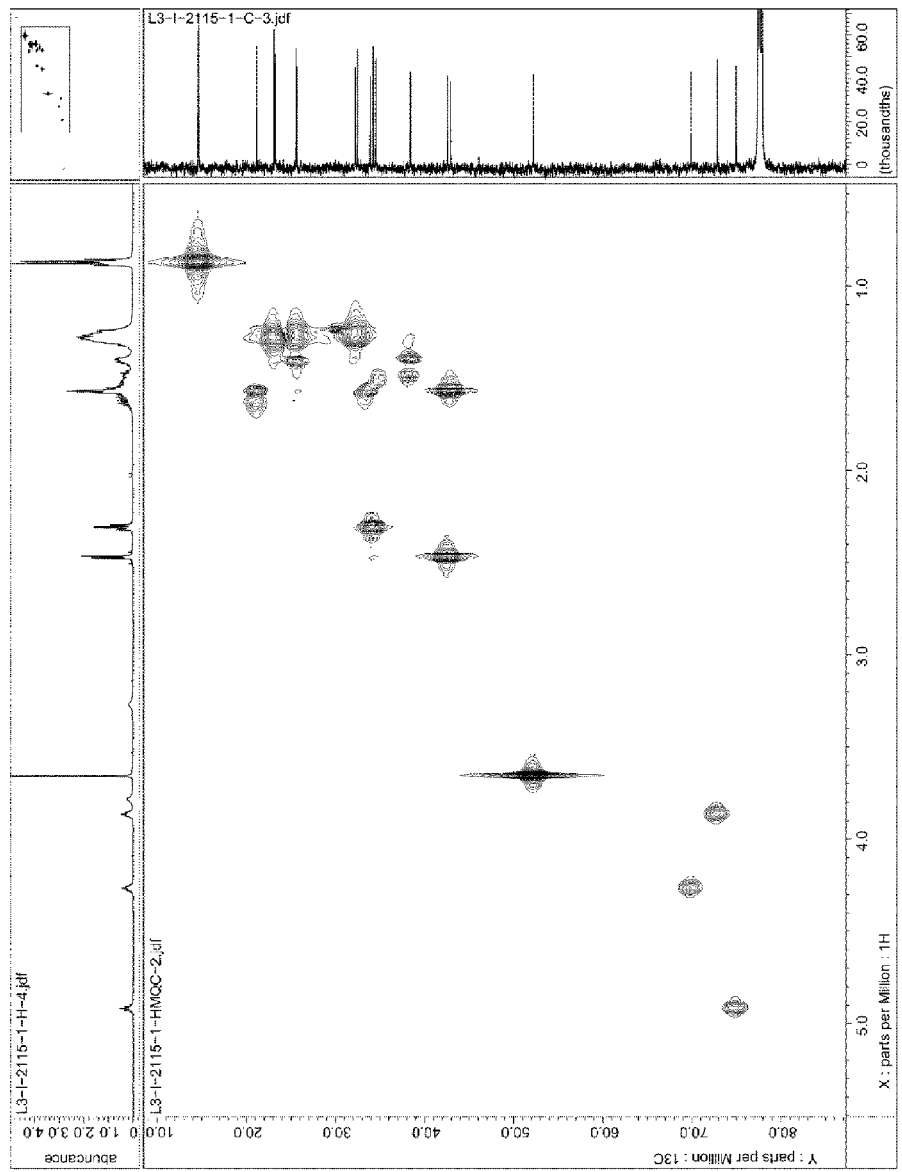
FIG. 16 is a HMQC spectrum of a compound L3-E6.

④ Measurement and Interpretation of HMQC and HMBC Spectra:

As a result of measuring a HMQC spectrum (FIG. 16), all proton-bearing carbons ($^1J_{C-H}$) were identified.

Figure 17:
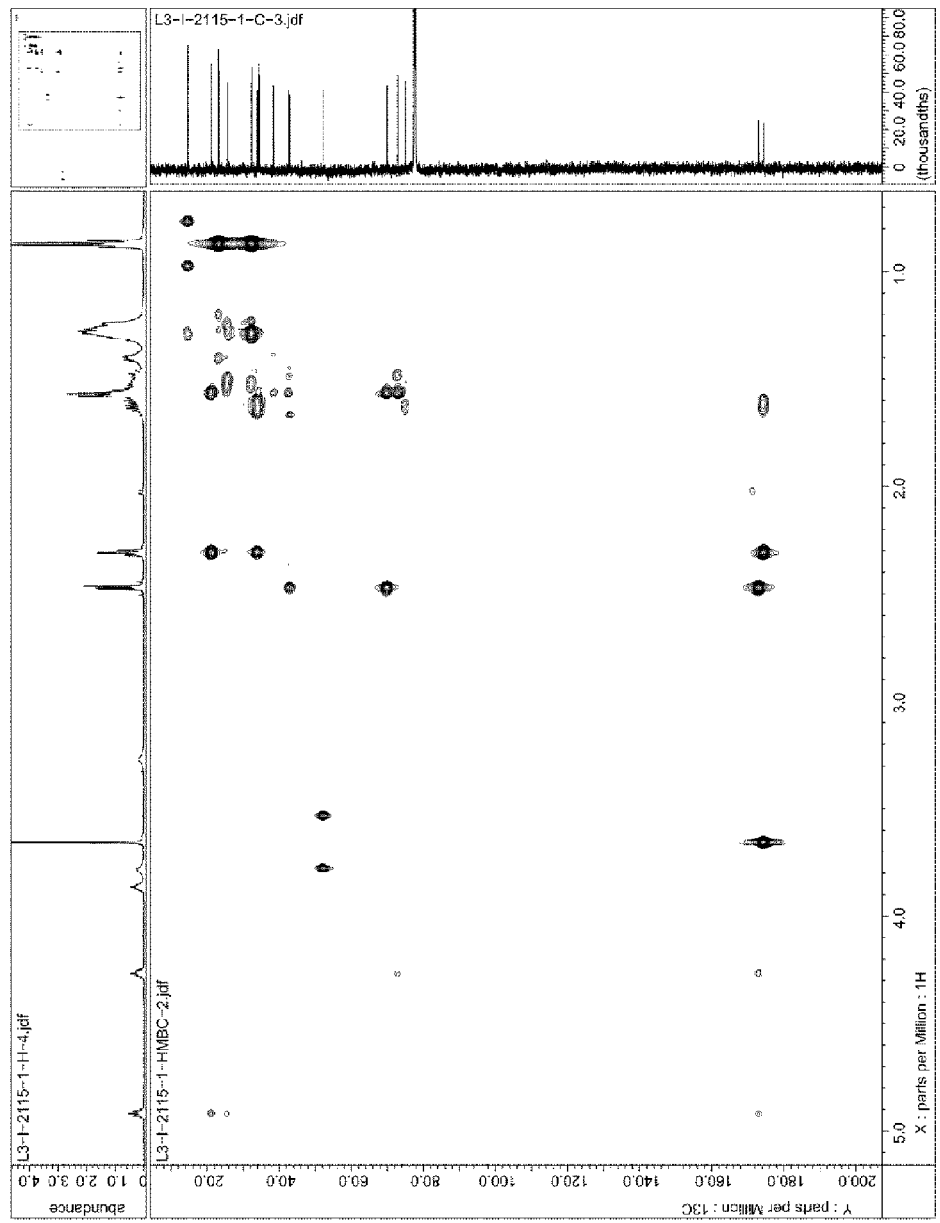
FIG. 17 is a HMBC spectrum of a compound L3-E6.
Figure 18:
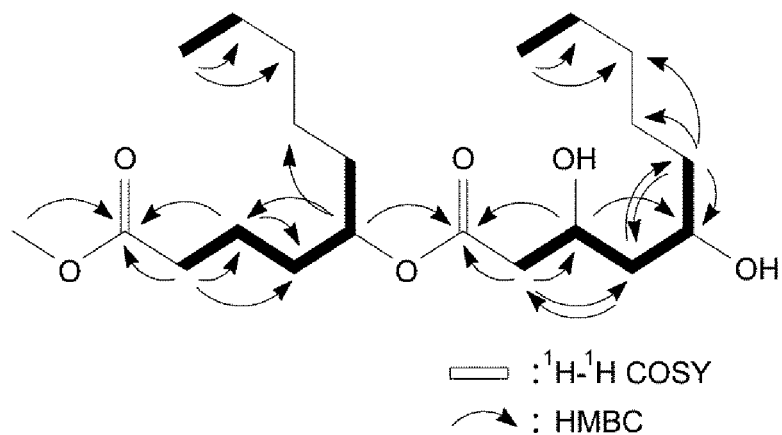
FIG. 18 is a chemical structure of a compound L3-E6 identified from the HMBC spectrum.
Figure 19:
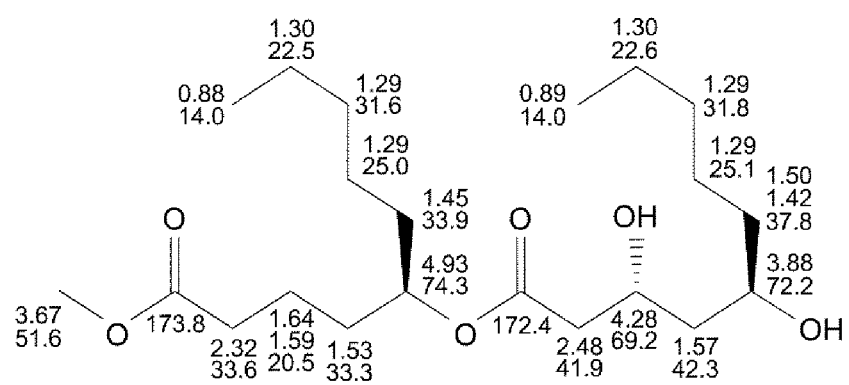
FIG. 19 is assignment values of $^1$H NMR and $^{13}$C NMR peaks of a compound L3-E6.

Further, as a result of measuring a HMBC spectrum (FIG. 17), a long-range correlation with an ester carbonyl carbon signal at 173.8 ppm was observed from a methoxy proton signal at 3.67 ppm and a methylene proton signal at 173.8 ppm, and a long-range correlation with an ester carbonyl carbon signal at 172.4 ppm was observed from an oxygenated methine proton signal at 4.93 ppm, a methylene proton signal at 2.48 ppm and an oxygenated methine proton signal at 4.28 ppm. These results suggest that two partial structures are connected. In two partial structures, a long-range correlation with a methylene carbon signal at 31.8 ppm was observed from a methylene proton signal at 1.50/1.42 ppm, and that with a methylene carbon signal at 31.8 ppm was observed from a methylene proton signal at 0.89 ppm. As a result of a removal process, it was confirmed that methylene carbon at 31.6 ppm was connected to methylene carbon at 25.0 ppm, which suggests that the compound L3-E6 has a chemical structure as illustrated in FIG. 18. FIG. 19 shows the reversion reaction of proton and carbon peaks of the compound L3-E6.

2) Measurement and Interpretation of Mass Spectrum

Figure 20:
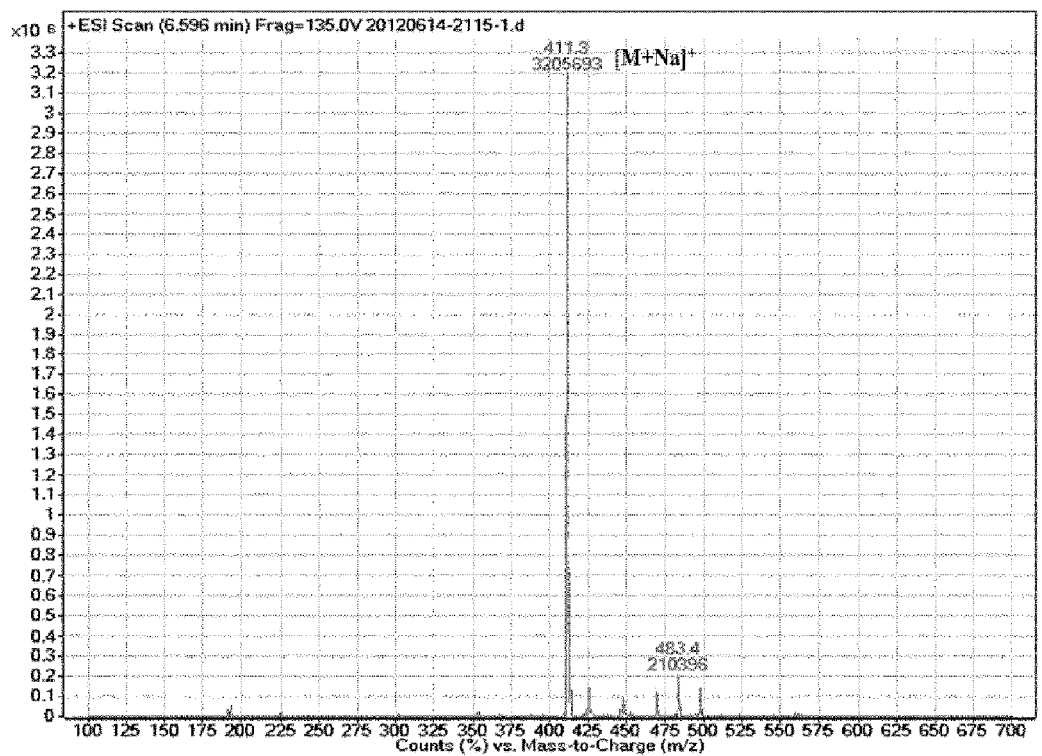
FIG. 20 is an ESI-mass spectrum of a compound L3-E6.

The chemical structure of the present active compound was identified by NMR spectroscopy. For this confirmation, mass spectroscopy analysis was carried out, and thus obtained results are as follows. As a result of measuring an ESI-mass spectrum in negative mode (FIG. 20), [M+H]$^+$ was observed at m/z 411.3, which suggests that the compound has a molecular weight of 308. This result corresponded to the chemical structure determined by the NMR spectroscopy (Molecular Formula: $C_{21}H_{40}O_6$).

EXAMPLE 7

Chemical Structure Analysis of Active Compound L3-E6 by Spectroscopy

1) Surface Tension Measurement

Figure 21:
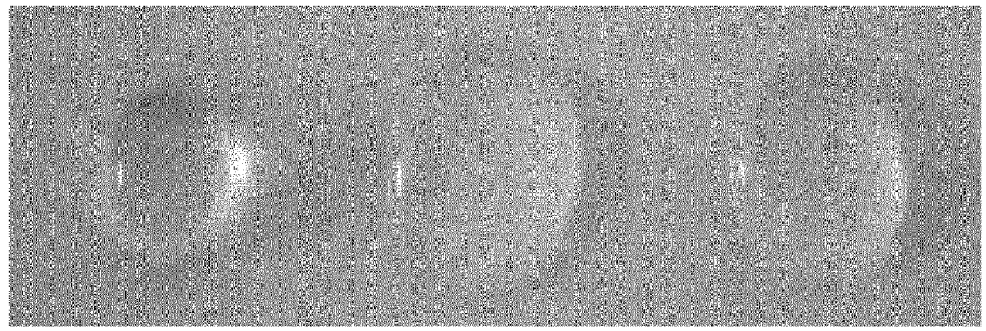
FIG. 21 is a photograph showing surface tension observed after an aqueous solution of the compound L3-E3 or L3-E6 is dropped onto a hydrophobic film.

The compounds L3-E3 and L3-E6 isolated in Examples 2 and 4, respectively, were dropped onto the surface of a hydrophobic film, and their surface tension was measured by using a tensiometer (Sigma 700 Tensiometer, KSV Instruments Ltd., Finland). Here, water was used as a control, and the change in surface tension was measured by using a microbial culture, L3-E3 and L3-E6. The results are shown in FIG. 21.

The novel compounds L3-E3 and L3-E6 according to the present invention showed a surface tension of 29.5 dyne/cm and 36.4 dyne/cm, respectively, at 1.0 mg/liter, such surface tension being relatively low.

DEPOSIT NUMBER

Deposit Authority: Korea Culture Center of Microorganism (domestic)
Accession Number: KCCM11200P
Deposit Date: 20110705

What is claimed is:

1. A compound represented by the following Formula 1

[Formula 1]

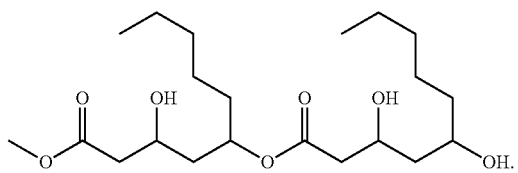

2. A compound represented by the following Formula 2

[Formula 2]

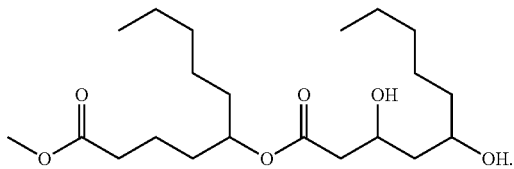

3. The compound according to claim 1, wherein the compound represented by the above Formula 1 is produced by *Aureobasidium pullulans* L-3-GPY deposited under Accession No. KCCM11200P.

4. The compound according to claim 2, wherein the compound represented by the above Formula 2 is produced by *Aureobasidium pullulans* L-3-GPY deposited under Accession No. KCCM11200P.

5. A biosurfactant comprising a compound represented by Formula 1

[Formula 1]

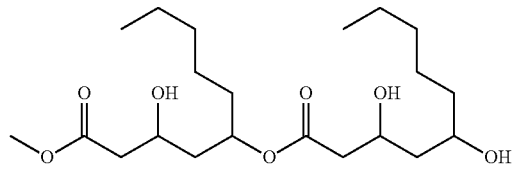

or Formula 2

[Formula 2]

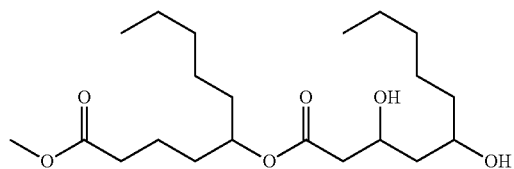

or a mixture thereof.

6. A cleansing and purifying composition comprising the biosurfactant according to claim 5.

7. A cosmetic composition comprising the biosurfactant according to claim 5.

* * * * *